United States Patent
Amer et al.

(10) Patent No.: US 6,331,075 B1
(45) Date of Patent: Dec. 18, 2001

(54) DEVICE AND METHOD FOR MEASURING THERMAL CONDUCTIVITY OF THIN FILMS

(75) Inventors: Tahani R. Amer, Yorktown, VA (US); Chelakara Subramanian, North East Palm Bay, FL (US); Billy T. Upchurch, Virginia Beach, VA (US); David W. Alderfer, Newport News, VA (US); Bradley S. Sealey, Newport News, VA (US); Cecil G. Burkett, Jr., Newport News, VA (US)

(73) Assignee: Administrator, National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/303,725

(22) Filed: Apr. 30, 1999

Related U.S. Application Data
(60) Provisional application No. 60/083,971, filed on May 1, 1998.

(51) Int. Cl.$^7$ .................................................. G01N 25/18
(52) U.S. Cl. ................................................................ 374/44
(58) Field of Search ........................................ 374/44, 43

(56) References Cited

U.S. PATENT DOCUMENTS

| | | | |
|---|---|---|---|
| 3,733,887 | 5/1973 | Stanley et al. | 374/44 |
| 4,568,198 | 2/1986 | Szabo et al. | 374/43 |
| 4,630,938 | 12/1986 | Piorkowska-Palczewska et al. | 374/44 |
| 4,928,254 | 5/1990 | Knudsen et al. | 702/136 |
| 4,929,089 | 5/1990 | Tsuchida | 374/44 |
| 4,944,035 | 7/1990 | Aagardi et al. | 702/136 |
| 4,978,229 | 12/1990 | Hughes | 374/30 |
| 5,005,985 | 4/1991 | Piorkowska-Galeska et al. | 374/44 |
| 5,010,250 | 4/1991 | Elsayed-Ali | 250/310 |
| 5,038,304 | 8/1991 | Bonne | 702/99 |
| 5,044,767 | 9/1991 | Gustafsson | 374/44 |
| 5,080,495 | 1/1992 | Hashimoto et al. | 374/43 |

(List continued on next page.)

OTHER PUBLICATIONS

T. Amer et al., "Thin–Film Thermal Conductivity Meter", *Instrument Society of America*, May 4, 1997.

E.H. Ratcliffe, "Thermal conductivities of fused and crystalline quartz", *British Journal of Applied Physics*, Jan. 1959.

(List continued on next page.)

*Primary Examiner*—John Barlow
*Assistant Examiner*—Stanley J. Pruchnic, Jr.
(74) *Attorney, Agent, or Firm*—Robin W. Edwards

(57) ABSTRACT

A device and method are provided for measuring the thermal conductivity of rigid or flexible, homogeneous or heterogeneous, thin films between 50 μm and 150 μm thick with relative standard deviations of less than five percent. The specimen is sandwiched between like material, highly conductive upper and lower slabs. Each slab is instrumented with six thermocouples embedded within the slab and flush with their corresponding surfaces. A heat source heats the lower slab and a heat sink cools the upper slab. The heat sink also provides sufficient contact pressure onto the specimen. Testing is performed within a vacuum environment (bell-jar) between $10^{-3}$ to $10^{-6}$ Torr. An anti-radiant shield on the interior surface of the bell-jar is used to avoid radiation heat losses. Insulation is placed adjacent to the heat source and adjacent to the heat sink to prevent conduction losses. A temperature controlled water circulator circulates water from a constant temperature bath through the heat sink. Fourier's one-dimensional law of heat conduction is the governing equation. Data, including temperatures, are measured with a multi-channel data acquisition system. On-line computer processing is used for thermal conductivity calculations.

18 Claims, 6 Drawing Sheets

U.S. PATENT DOCUMENTS

| | | | |
|---|---|---|---|
| 5,099,441 | 3/1992 | Mazzio | 702/136 |
| 5,112,136 | 5/1992 | Sakuma et al. | 374/44 |
| 5,251,980 | 10/1993 | Hiraoka et al. | 374/7 |
| 5,258,929 | 11/1993 | Tsuchida | 702/136 |
| 5,295,389 | 3/1994 | Nagata et al. | 73/25.03 |
| 5,297,868 | 3/1994 | Graebner | 374/44 |
| 5,335,993 | 8/1994 | Marcus et al. | 374/11 |
| 5,377,527 | 1/1995 | Kamiunten | 73/25.03 |
| 5,558,790 | 9/1996 | Nazarian | 219/121.77 |
| 5,667,301 | 9/1997 | Jurkowski et al. | 374/43 |
| 5,688,049 | 11/1997 | Govorkov | 374/44 |
| 5,940,784 * | 8/1999 | El-Husayni | 374/43 |
| 6,142,662 * | 11/2000 | Narh et al. | 374/44 |

OTHER PUBLICATIONS

ASTM Standard D5470–95, Nov. 1995.

ASTM Standard E1225–87, (Feb. 1988).

ASTM Standard C518–91, (Sep. 1991).

ASTM Standard E1530–93, (Dec. 1993).

International Thermal Instrument Company Specifications for Models C–2500–HTS, (Jun. 1996).

International Thermal Instrument Company Data Sheet 439 (No Date).

International Thermal Instrument Company Data Sheet 440 (No Date).

International Thermal Instrument Company Bulletin H–45, (No Date).

International Thermal Instrument Company Bulletin C 397, (No Date).

International Thermal Instrument Company Bulletin H–33, (No Date).

International Thermal Instrument Company Photo B–8881, (No Date).

Anter Corporation Product Specifications for Models 2021, 2031, 2101, and QL–10, (Apr./1999).

* cited by examiner

DEVICE AND METHOD FOR MEASURING THERMAL CONDUCTIVITY OF THIN FILMS

CLAIM OF BENEFIT OF PROVISIONAL APPLICATION

Pursuant to 35 U.S.C. §119, the benefit of priority from provisional application No. 60/083,971, with a filing date of May 1, 1998, is claimed for this non-provisional application.

ORIGIN OF THE INVENTION

The invention described herein was jointly made by employees of the United States Government and a NASA Grant employee during the performance of work under NASA Grant No. NGT-1-52122.

BACKGROUND OF THE INVENTION

1. Field of the Invention

This invention relates to a device and a method for measuring the thermal conductivity of thin films of materials, and more particularly a method and device for measuring the thermal conductivity of rigid or flexible, homogeneous or heterogeneous, thin films between 50 μm and 150 μm thick with relative standard deviations of less than five percent.

2. Description of the Related Art

NASA is developing Temperature Sensitive Paints (TSP's) for global non-intrusive detection of boundary layer transition in flow over the surface of wind tunnel research models. The TSP sensitivity should be large enough to resolve the smallest amplitude and the highest frequency fluctuations, since the transition process involves unsteady fluctuations. Based on linear steady-state heat transfer analysis, one of the steps to improve the paint sensitivity is minimizing the thermal conductivity of the paint. The TSP applied to wind tunnel research models is typically 25 μm to 125 μm thick with an additional 25 μm thick primer layer. The TSP's are typically composed of metal complexes in polymer binders. A thermal conductivity measuring device is needed to measure thermal conductivity of the TSP's and accompanying primer layer, which are typically between 50 μm and 150 μm total thickness.

Existing thermal conductivity measuring devices are suitable only for very thin (<20 μm) or very thick (>6.25 mm) specimens. Ultrasonic principles have been used to measure film thicknesses less than 20 μm, but such principles require a priori knowledge of the material's specific heat and density to determine the thermal conductivity. These devices target silicon dioxide films suitable for microelectronics, micromechanics, micro-optics, and semiconductor processing. Devices marketed to measure thicker specimens (>6.25 mm), such as insulations, composites, cloth, natural fibers such as wood, generally have difficulty attaining one-dimensional conduction. The alternating current technique measures thermal conductivity of bulk gases, but a modified technique measures thin films and is referred to as the 3-ω technique, discussed in D. G. Cahill, H. E. Fischer, T. Klitsner, E. T. Swartz, and R. O. Pohl, "Thermal Conductivity of Thin Films: Measurements and Understanding", American Vacuum Society, 1989. Other techniques have also been used to make thin film thermal conductivity measurements: thermal comparators, such as described in R. W. Powell, "Experiments using a simple thermal comparator for measurement of thermal conductivity, surface roughness and thickness of foils or surface deposits", J. Sci. Instrum., 1957; specialized film geometries, such as described in B. T. Boiko, A. T. Pugachev, and V. M. Bratsychin, "Method for the determination of the thermophysical properties of evaporated thin films", Thin Solid Films, 1973; laser calorimetry, such as set forth in D. Ristau, and J. Ebert, "Development of a thermographic laser calorimeter", Appl. Opt., 1986; and flash radiometry, such as set forth in N. Tsutsumi, and T. Kiyotsukuri, "Measurement of thermal diffusivity for polymer film by flash radiometry", Appl. Phys. Lett., 1988. The steady-state test methods described in ASTM Standards E1530-93 and D5470-95 are applicable to stacked thin-film specimens that are homogeneous. Stacking would be required for thin films 50 μm 150 μm thick. Thermal conductivity varies with thickness so stacking introduces measurement inaccuracies. The steady state test method described in ASTM Standard E1225 is applicable to homogeneous, opaque specimens and has a thermocouple design, which introduces inaccuracies into the thermal conductivity measurement.

The conventional types of thermal conductivity meters have the problems of heat losses, contact resistance losses, and large inaccuracies. Furthermore, existing mathematical (empirical) models for determining the thermal conductivity of thin films are not very reliable, especially over a wide range of pressures and temperatures. Therefore, a measurement technique is needed to measure, both steady state and transient, the thermal conductivity of thin films of materials, such as paints, that are 50–150 μm thick, with relative standard deviations of less than five percent.

SUMMARY OF THE INVENTION

Accordingly, it is an object of the present invention to provide a thermal conductivity measurement device and method that can measure thermal conductivity of films 50 μm to 150 μm thick.

It is another object to provide a thermal conductivity measurement device and method that can measure thermal conductivity of films 50 μm to 150 μm thick with relative standard deviations of less than five percent.

It is another object to provide a thermal conductivity measurement device and method that minimizes heat losses.

It is a further object to provide a thermal conductivity measurement device and method to simulate test temperatures in the range of −200 C. to 100 C.

It is a further object to provide a thermal conductivity measurement device and method to simulate test pressures up to five atmospheres.

It is yet another object to provide a thermal conductivity measurement device and method that provides a uniform heat transfer area to the specimen.

It is yet another object to provide a thermal conductivity measurement device and method that provides a large, uniform heat transfer area to the specimen via well-polished surfaces.

It is yet another object to provide a thermal conductivity measurement device and method that operates in both steady state and transient heat conduction modes.

It is yet another object to provide a thermal conductivity measurement device and method that has minimal lateral conduction loss.

It is yet another object to provide a thermal conductivity measurement device and method that has a very low operating test environment pressure.

It is yet another object to provide a thermal conductivity measurement device and method that has a test environment pressure between approximately $10^{-3}$ to $10^{-6}$ Torr.

It is yet another object to provide a thermal conductivity measurement device and method having ease of fabrication and use.

Other objects and advantages of the present invention will become more obvious hereinafter in the specification and drawings.

In accordance with the present invention, a device and method are provided for measuring the thermal conductivity of rigid or flexible, homogeneous or heterogeneous, thin films between 50 μm and 150 μm thick with relative standard deviations of less than five percent. The specimen is sandwiched between like material, highly conductive upper and lower slabs. Each slab is instrumented with six thermocouples embedded within the slab and flush with their corresponding surfaces. A heat source heats the lower slab and a heat sink cools the upper slab. The heat sink also provides sufficient contact pressure onto the specimen. Testing is performed within a vacuum environment (bell-jar) between approximately $10^{-3}$ to $10^{-6}$ Torr. An anti-radiant shield on the interior surface of the bell-jar is used to avoid radiation heat losses. A temperature controlled water circulator circulates water from a constant temperature bath through the heat sink. It is also preferable to use insulation adjacent to the heat source and adjacent to the heat sink to prevent conduction losses. Fourier's one-dimensional law of heat conduction is the governing equation. Data, including temperatures, are measured with a multi-channel data acquisition system. On-line computer processing is used for thermal conductivity calculations.

DETAILED DESCRIPTION OF THE INVENTION

Figure 1:
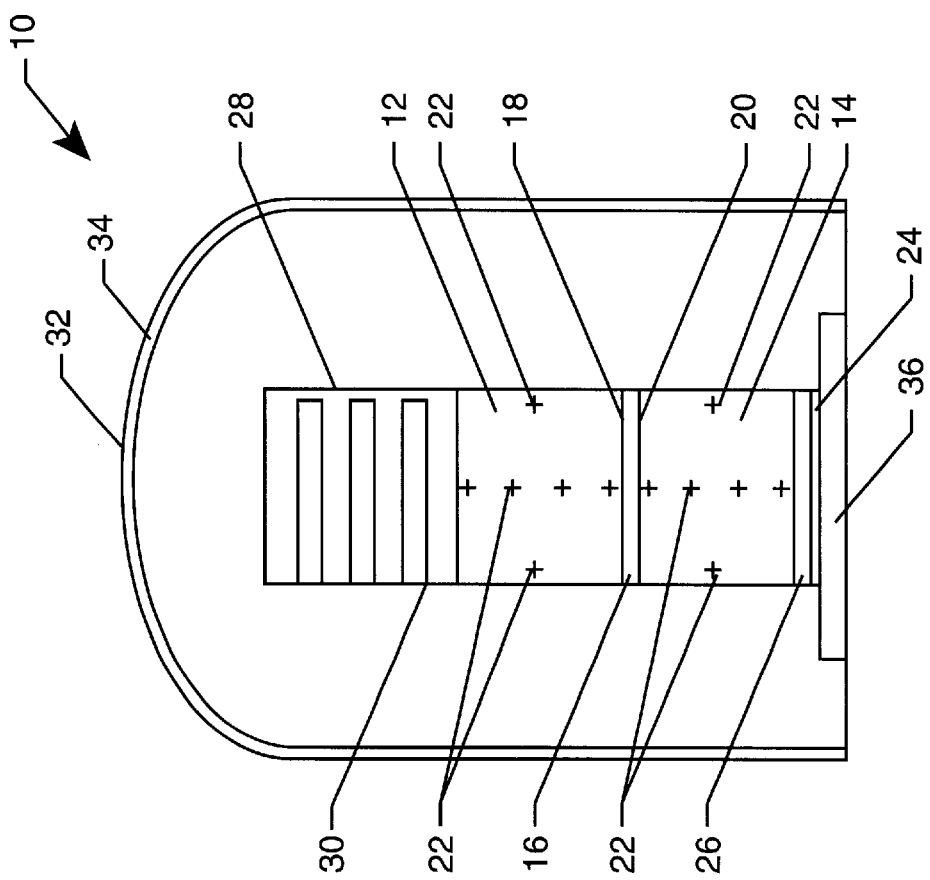
FIG. 1 is a schematic diagram of the specimen set-up and environment.

Referring now to the drawings and more particularly to FIG. 1, the specimen set-up and environment of the present invention are shown and referenced generally by numeral 10. Two slabs 12 and 14, 12 being the upper and 14 being the lower, are used to sandwich the test specimen 16. The same material is used for both slabs 12 and 14 and the material should be highly conductive, preferably aluminum. A cylindrical cross section is preferred. Specifically, two aluminum, Type-2024, 51 mm (2 in) diameter by 51 mm (2 in) long slabs have been used successfully experimentally, as are preferred. The specimen sides 18 and 20 of the slabs 12 and 14 are polished, preferably to 5 microns, to maximize surface contact. Where the measurement of the thermal conductivity of a paint is desired, the paint and associated primer can be sprayed directly onto the surface of a slab, preferably the upper surface of the lower slab 14.

Figure 2:
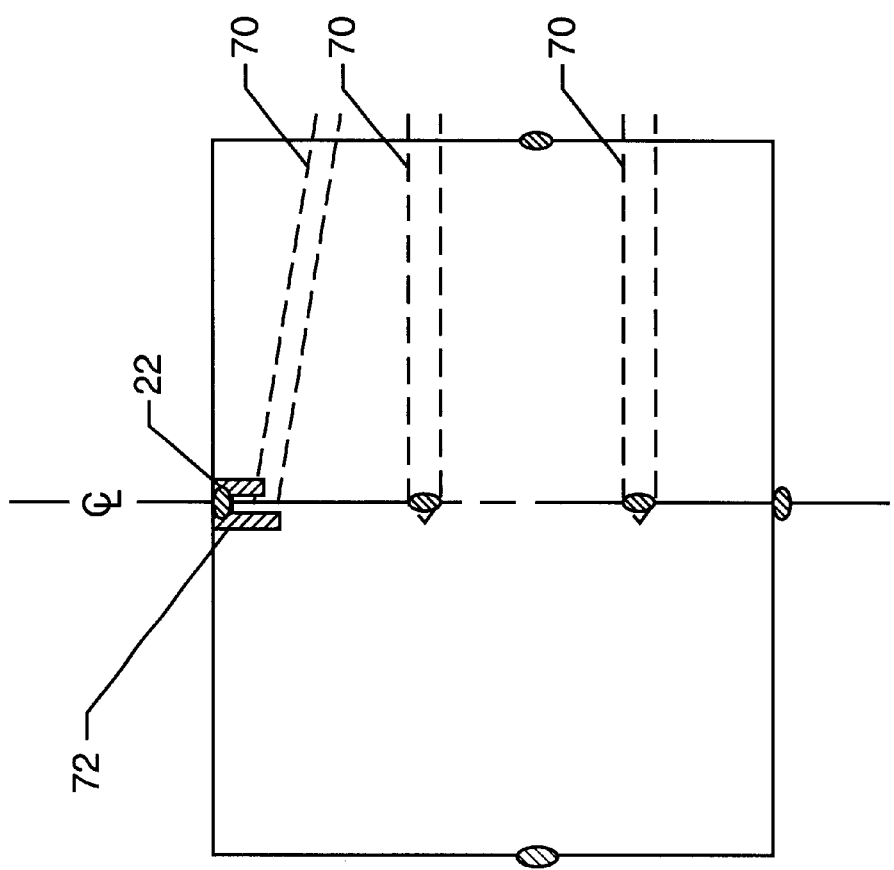
FIG. 2 is a schematic diagram of thermocouple installation.

Each slab 12 and 14 is instrumented with six thermocouples 22: four surface thermocouples (one thermocouple embedded in each of the top and bottom surfaces and one thermocouple embedded on each of the diametrically opposite sides at half slab) and two embedded thermocouples equidistance along the axial center line of each slab. Each thermocouple is mounted flush with its corresponding slab surface. For a 51 mm (2 in) diameter by 51 mm (2 in) long slab, the center line thermocouples would be positioned 12.74 mm (0.5 in) from each of the top and bottom surfaces of each slab. The size, time response and resolution of the thermocouples are important. ANSI Type T (Copper-Constantan 36 AWG wire) thermocouples are preferred. Further details of the thermocouple installation in the slabs 12 and 14 are shown in FIG. 2. The hole 70 for each thermocouple wire is filled with a filler of the same conductivity as the slabs 12 and 14. An insert is used to allow for flush mounting of thermocouple 22 located adjacent to specimen 16. For a 2 in. long, 2 in. diameter slab, a hole size of 1/24 in. diameter is typical. FIG. 2 is a schematic, and is not a "to scale" representation.

A heat source 24, preferably a 31.4 watt foil heater, is attached to a copper disk 26 on which the bottom slab 14 rests. A copper block 28 is placed on the top of upper slab 12 to provide sufficient contact pressure onto the specimen 16. The copper block 28 also acts as a heat sink and has an internal circular groove passageway 30 in which copper tubing, preferably ¼ in, is inserted and soldered into place to circulate cooling water.

Several design features are incorporated to minimize heat loss. The aforementioned structure and sandwiched specimen 16 are placed in and thermal conductivity tests are performed inside a bell-jar 32 evacuated to a very low pressure, between approximately $10^{-3}$ and $10^{-6}$, to avoid convective heat losses. The entire interior surface of the bell jar 32 is coated with an anti-radiant material 34, such as aluminum foil, to avoid radiation heat losses. Conduction losses from the bottom of the foil heater 24 are minimized by an insulated pad 36, preferably foam.

Figure 3:
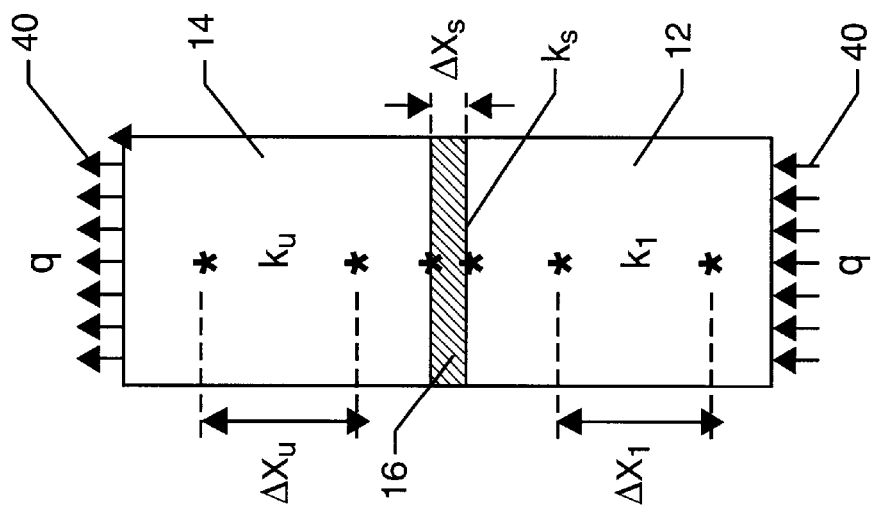
FIG. 3 is a schematic diagram of the heat flow mechanics.

Referring to FIG. 3, the heat transfer mode is one-dimensional (1-D) conduction (infinite slab), where heat transfers from the higher to the lower temperature region across the specimen. Fourier's law of heat conduction is the governing equation. Thermal conductivity of the specimen 16, $k_s$ (w/(m° K)), is defined by the heat flux q (watts/m²) through the specimen, the temperature difference across the specimen, $\Delta T_s$ (°K), and the thickness of specimen, $\Delta x_s$ (m). The equations are:

$$k_s = (q \Delta x_s)/(\Delta T_s) \qquad (1)$$

where q is given by:

$$q = 0.5 \left[ \frac{k_1 \Delta T_1}{\Delta x_1} + \frac{k_u \Delta T_u}{\Delta x_u} \right] \qquad (2)$$

and wherein $k_1$ (w/(m° K)) and $k_u$ (w/(m° K)) are the thermal conductivities of the lower and upper slabs 14 and 12 respectively, $\Delta T_1$ (°K) and $\Delta T_u$ (°K) are the temperatures of the lower and upper slabs 14 and 12 respectively, $\Delta x_1$ (m) and $\Delta x_u$ (m) are the distances between the two center line thermocouples of the lower and upper slabs 14 and 12 respectively.

To calculate the ideal heat flux $q_i$ in the system, one can calculate the voltage and the current that is applied to the heater 24. If there is no heat loss of any kind in the system, the ideal heat flux $q_i$ should equal the calculated heat flux in the upper and lower slabs 12 and 14. The arrows 40 in FIG. 3 show the heat flow direction. The equation for the ideal heat flux $q_i$ is:

$$q = \frac{k_l \Delta T_l}{\Delta x_l} = \frac{k_u \Delta T_u}{\Delta x_u} = (V)(I) \qquad (3)$$

where V and I are the voltage and current, respectively, supplied to the heater.

Figure 4:
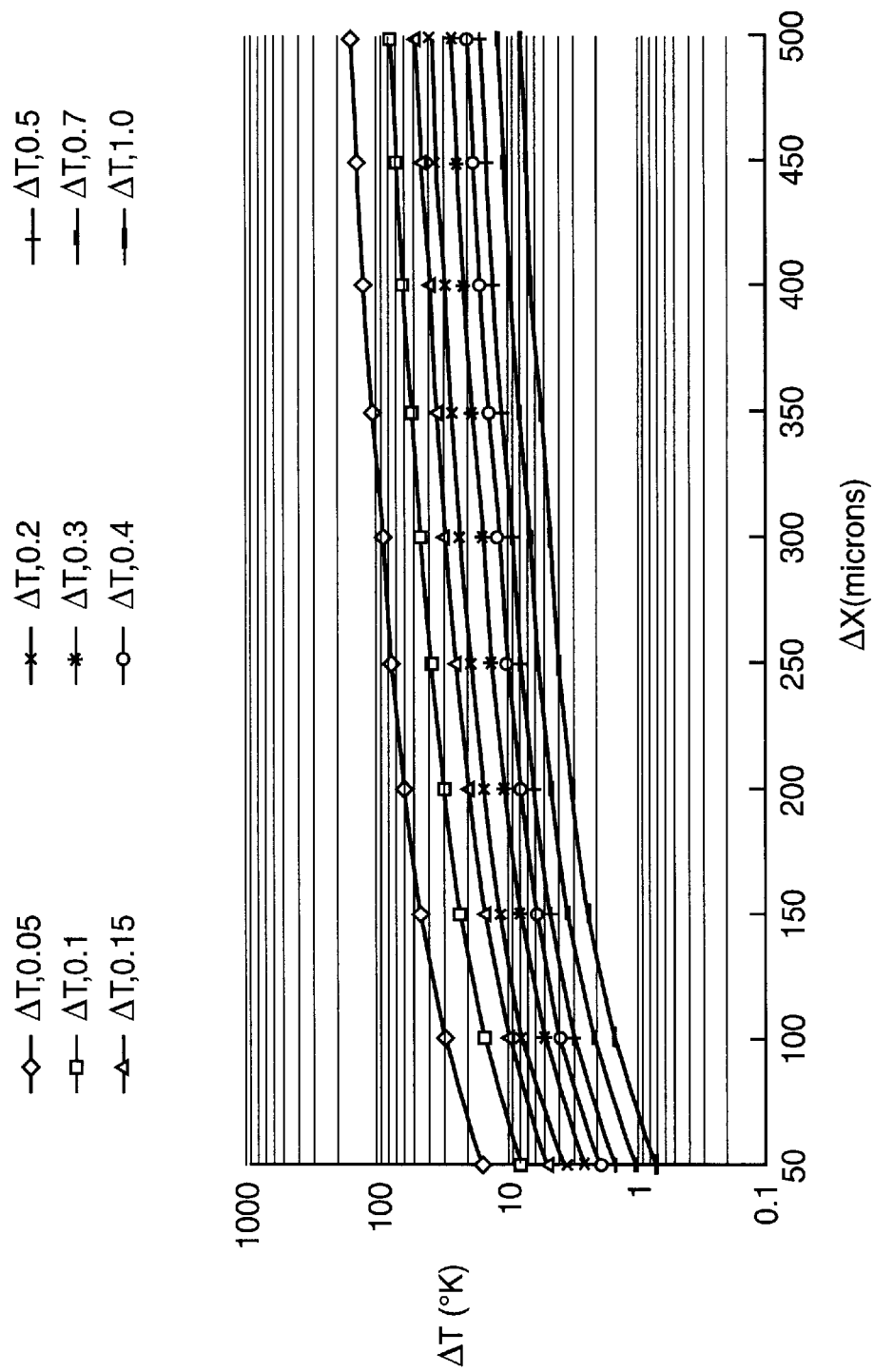
FIG. 4 is a graphical representation of the temperature difference across a specimen versus thickness of the specimen for various thermal conductivities.

The calculated theoretical plots, shown in FIG. 4, for different thermal conductivity suggest that the temperature difference across the specimen 16 decreases with specimen thickness for high conductivity materials. This small temperature difference may pose a measurement problem for such materials, especially if the resolution limit of the thermocouples is reached. Therefore, thermocouples with a sufficiently small size and high resolution must be used in order to accurately measure the small temperature differences.

Figure 5:
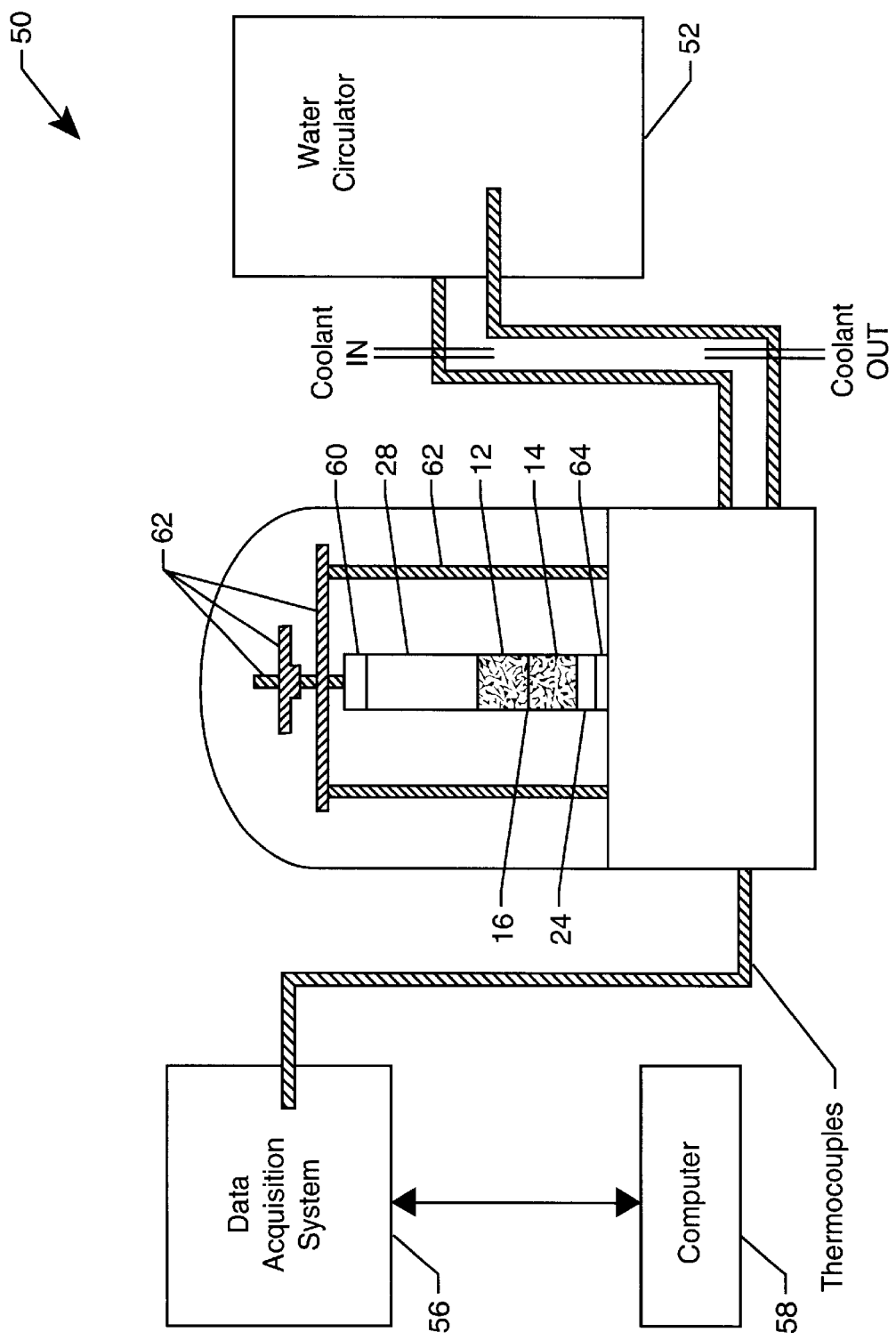
FIG. 5 is a schematic diagram of the overall thermal conductivity measurement lay-out.

FIG. 5 is a schematic representation of the overall layout 50, of the thermal conductivity measurement device. A temperature controlled water circulator 52 is used to circulate water from a constant temperature bath through heat sink 28. The set-point temperature of the bath is determined by the test temperature, and is such to enable an accurate $\Delta T_s$ measurement across the specimen. The coolant flow rate is set to maintain the block temperature at the same temperature of the bath. When necessary, additional weights can be placed on the copper block 28 for high pressure testing. The pressure on the specimen 16 is determined from the weights of the upper slab 12 and the copper block 28. All temperatures are measured with a multi-channel data acquisition system 56, such as a Fluke Hydra system and processed using on-line computer 58 processing. Steady-state heat flux through the specimen 16 is determined from the average temperature gradients in the upper and lower slabs 12 and 14 respectively. The thermal conductivity of the slab material is obtained from a standard reference, such as, for Aluminum-2024, the Alloy Digest, Aluminum-2024 Material Data Sheet, published by Engineering Alloys Digest, Inc., August 1973. For transient heat conduction experiments, the heat input is measured from the voltage and current supplied to the heater 24. Insulation 60 and 64, such as foam, is used to prevent conduction losses. A support structure 62 provides support for the columnar assembly.

The thermal conductivities of four standard thin-film materials; Kapton®-HN, Kapton®-MT, Teflon®, and Borofloat™glass; were determined (steady state) with the experimental arrangement shown in FIG. 3. In these tests, a very thin layer of thermal grease was applied between the specimen and the upper and lower slabs 12 and 14 respectively to provide good contact. Table I summarizes the manufacturers' and measured thermal conductivity values for the samples measured. The agreement between the two values is within ±5%. These thermal conductivity values were repeatable within acceptable uncertainty limits.

TABLE I

| Specimen Name | Thickness (μm) | Manufacture Name | Manufacture Spec. $k_s$ (w/m° K) | Measured Value $k_s$ (w/m° K) |
|---|---|---|---|---|
| 1. Kapton ®-HN | 76 | Du-Pont[10] | 0.145–0.155 (reference Du-Pont-Kapton Material Data Sheet, 1995) | 0.148 |
| 2. Kapton ®-MT | 76 | Du-Pont[10] | 0.46–0.52 (reference Du-Pont-Kapton Material Data Sheet, 1995) | 0.449 |
| 3. Borofloat ™ Glass | 1110 | Schottt Corp. | 1.027–1.113 | 1.0922 |

An uncertainty analysis was performed to determine system performance and system calibration using the data acquired from the Kapton®-HN standard specimens. The analysis was done in several steps using modern experimental design analysis.

First, the dominating sources of error were identified using general uncertainty analysis. The governing equation is:

$$(q = k_s \Delta T_s / \Delta x_s) \qquad (4)$$

The uncertainty equation is:

$$U_q = [\{(\partial q/\partial k_s) U_{ks}\}^2 + \{(\partial q/\partial \Delta T_s) U_{\Delta Ts}\}^2 + \{(\partial q/\partial \Delta x_s) U_{\Delta xs}\}^2]^{1/2} \qquad (5)$$

where $U_{(\ )}$ denotes the uncertainty of that variable, $\Delta T_s$ is the temperature difference (°K) through the specimen, $\Delta k_s$ is the thermal conductivity (W/m° K) of the sample, and $\Delta x_s$ is the specimen thickness (m).

Taking the derivatives and simplifying, $$(U_{ks}/k_s)^2 = (U_q/q)^2 + (U_{\Delta Ts}/\Delta T_s)^2 + (U_{\Delta xs}/\Delta_{xs})^2 \qquad (6)$$

where q and $\Delta T_s$ are relatively large numbers compared to $\Delta x_s$, thus $\Delta x_s$ is the dominating variable in this measurement.

Next, the effect of the change in the thickness of the specimen 16 was identified. The method used was to obtain three replicated analyses on the same sample, each containing 30 data points. The test (steady-state) was conducted using three different thicknesses, 1, 3, and 5 mils, of Kapton®-HN . Table II summarizes the standard deviation results.

TABLE II

| Sample Thickness | Kapton ®-HN 25 μm (1 mil) | Kapton ®-HN 75 μm (3 mils) | Kapton ®-HN 125 μm (5 mils) | Manufacture value |
|---|---|---|---|---|
| $k_s$ (w/m° K) | 0.144 | 0.148 | 0.156 | 0.145–0.155 |
| Std. DEV. | 0.002 | 0.002 | 0.002 | |

Figure 6:
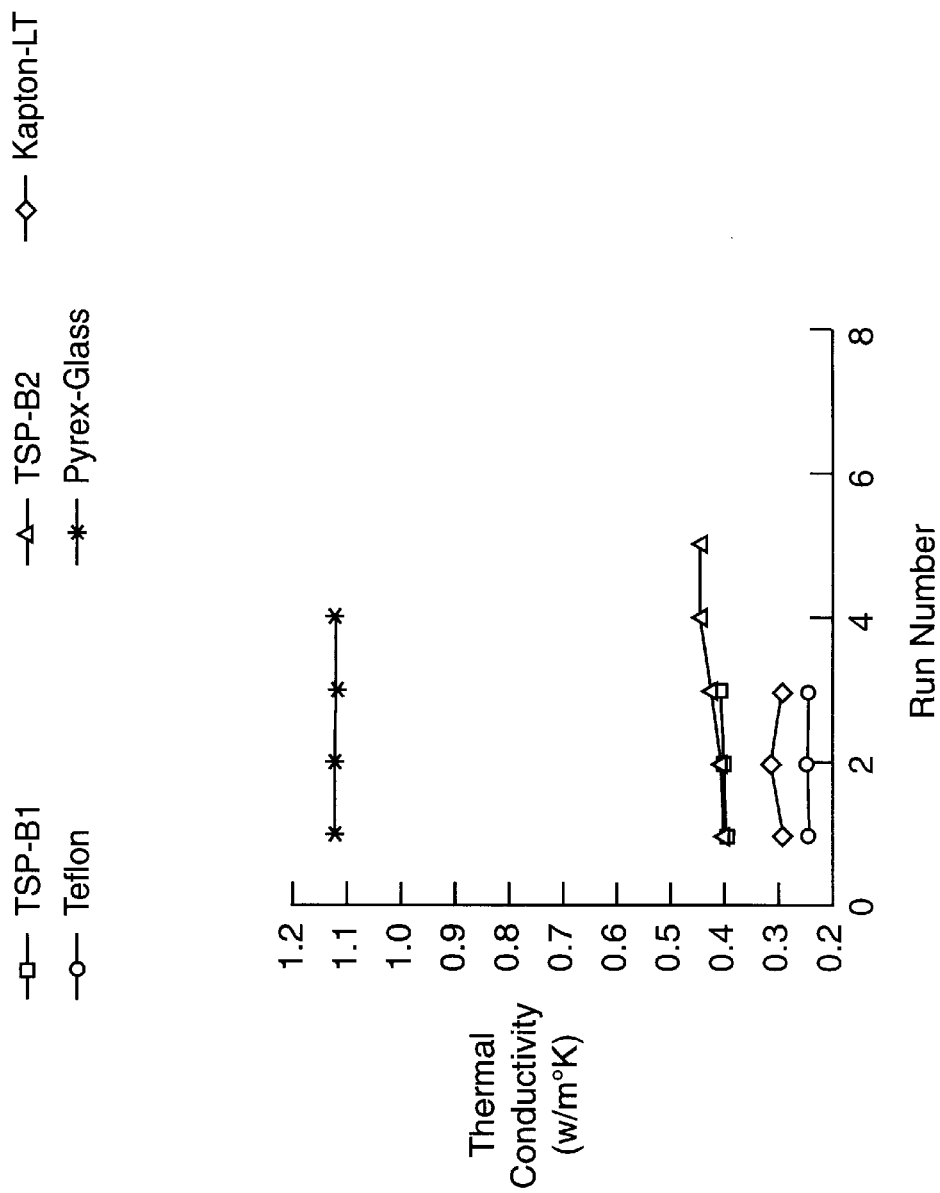
FIG. 6 is a graphical representation of thermal conductivities for various materials.

The schematic of FIG. 5 was also used to measure (steady state) the thermal conductivity of TSP's. Two proprietary TSP specimens of the same material having film thicknesses of 75 μm and 100 μm were prepared on a copper coupon 1 mm thick. The copper coupon was used to provide some rigidity to the TSP films, and to facilitate both preparation of the film outside the test set-up and transfer to the test set-up. Since the thermal conductivity of the copper coupon is several orders of magnitude greater than that of the TSP film, the temperature difference across the coupon was assumed to be negligible as compared to that across the TSP. The average value of $k_s$ was found to be 0.41±0.02 (w/m° K) for these specimens. FIG. 6 shows graphical results for the two TSP's as well as for Kapton®-LT, Teflon® and Pyrex® Glass.

Although the invention has been described relative to certain specific embodiments thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

We claim:

1. A device for measuring the thermal conductivity of a sample, comprising:
   an upper slab and a lower slab, said upper slab adjacent to the upper surface of said sample and said lower slab adjacent to the lower surface of said sample, said upper and lower slabs sandwiching said sample in a columnar arrangement, said sample and said slabs forming a sandwiched assembly;
   a heat source for heating said lower slab;
   a heat sink for cooling said upper slab and for providing contact pressure onto said specimen;
   said upper and lower slabs, said heat source, and said heat sink forming a sandwiched assembly;
   a plurality of thermocouples embedded within and flush with the surfaces of said upper and lower slabs, for measuring the temperature difference across said specimen, further wherein said plurality of thermocouples comprise, at least, one thermocouple embedded at the center of each of the upper and lower surfaces of said upper and lower slabs, one thermocouple embedded at the center of each of the diametrically opposite outer exposed surfaces of said upper and lower slabs, and two thermocouples embedded equidistance along the axial center line within each said upper and lower slabs;
   insulation means placed at each axial end of said sandwiched assembly to prevent conduction losses;
   a measuring chamber enclosing said sandwiched assembly and said insulation means, said measuring chamber comprising a vacuum environment having a pressure between approximately $10^{-3}$ to $10^{-6}$ Torr;
   an anti-radiant shield disposed on the entire interior periphery of said measuring chamber;
   a temperature controlled water circulator for transferring and receiving water from said heat sink; and
   a multi-channel data acquisition means for acquiring and supplying data to an on-line computer processing means; wherein said on-line computer processing means processes said data.

2. The device of claim 1, wherein said sample is a thin film having a thickness between 50 µm and 150 µm.

3. The device of claim 1, wherein said surfaces of said upper and lower slabs adjacent to said sample are polished to 5 microns.

4. The device of claim 1, wherein said upper and lower slabs are aluminum.

5. The device of claim 1, wherein said heat sink is a copper block having internally flowing cooling water, said copper block positioned adjacent to the upper surface of said upper slab.

6. The device of claim 1, wherein said heat source is a foil heater.

7. The device of claim 1, further comprising a copper disk between said foil heater and said lower slab.

8. The device of claim 1, further comprising a conductive material applied between said specimen and corresponding adjacent surfaces of said upper and lower slabs to aid surface contact between said slabs and said specimen.

9. The device of claim 1, further comprising additional weight applied to said upper slab, thereby increasing the pressure applied to said sample.

10. A method for measuring the thermal conductivity of a sample, comprising the steps of:
    sandwiching said sample between an upper slab and a lower slab in a columnar arrangement, said upper slab adjacent to the upper surface of said sample, and said lower slab adjacent to the lower surface of said;
    providing a heat source for heating said lower slab;
    providing a heat sink for cooling said upper slab and for providing contact pressure onto said specimen;
    said upper and lower slabs, said heat source, and said heat sink forming a sandwiched assembly;
    placing an insulation means at each axial end of said sandwiched assembly to prevent conduction losses;
    enclosing said sandwiched assembly and insulation means with a measuring chamber, said measuring chamber comprising a vacuum environment having a pressure between approximately $10^{-3}$ to $10^{-6}$ Torr, said measuring chamber further comprising an anti-radiant shield on its entire interior periphery;
    circulating cooling water through said heat sink using a temperature controlled water circulator;
    measuring the temperature difference across said specimen using a plurality of thermocouples embedded within and flush with the surfaces of said upper and lower slabs, further wherein said plurality of thermocouples comprise, at least, one thermocouple embedded at the center of each of the upper and lower surfaces of said upper and lower slabs, one thermocouple embedded at the center of each of the diametrically opposite outer exposed surfaces of said upper and lower slabs, and two thermocouples embedded equidistance along the axial center line within each said upper and lower slabs;
    acquiring data using a multi-channel data acquisition means;
    supplying data from said data acquisition means to an on-line computer processing means for data processing.

11. The method of claim 10, wherein said sample is a thin film having a thickness between 50 µm and 150 µm.

12. The method of claim 10, wherein said surfaces of said upper and lower slabs adjacent to said sample are polished to 5 microns.

13. The method of claim 10, wherein said upper and lower slabs are aluminum.

14. The method of claim 10, wherein said heat sink is a copper block having internally flowing cooling water, said copper block positioned adjacent to the upper surface of said upper slab.

15. The method of claim 10, wherein said heat source is a foil heater.

16. The method of claim 10, further comprising the step of providing a copper disk between said foil heater and said lower slab.

17. The method of claim 10, further comprising the step of applying a conductive material between said specimen and corresponding adjacent surfaces of said upper and lower slabs to aid surface contact between said slabs and said specimen.

18. The method of claim 10, further comprising the step of applying additional weight to said upper slab, thereby increasing the pressure applied to said sample.

* * * * *